US012622630B2

(12) United States Patent
    Kim et al.

(10) Patent No.: US 12,622,630 B2
(45) Date of Patent: May 12, 2026

(54) APPARATUS FOR MOTOR IMAGERY TRAINING COMBINED WITH SOMATOSENSORY STIMULI AND OPERATION METHOD THEREOF

(71) Applicant: KOREA INSTITUTE OF SCIENCE AND TECHNOLOGY, Seoul (KR)

(72) Inventors: Laehyun Kim, Seoul (KR); Jihyeon Ha, Seoul (KR); Sangin Park, Seoul (KR); Da-Hye Kim, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 581 days.

(21) Appl. No.: 18/326,242

(22) Filed: May 31, 2023

(65) Prior Publication Data

US 2024/0138748 A1 May 2, 2024

(30) Foreign Application Priority Data

Nov. 1, 2022 (KR) ........................ 10-2022-0144020

(51) Int. Cl.
     *A61B 5/00* (2006.01)
     *A61B 5/372* (2021.01)

(52) U.S. Cl.
     CPC ............ *A61B 5/4005* (2013.01); *A61B 5/372* (2021.01); *A61B 5/7203* (2013.01)

(58) Field of Classification Search
     CPC ...... A61B 5/4005; A61B 5/372; A61B 5/7203
     See application file for complete search history.

(56) References Cited

U.S. PATENT DOCUMENTS 6,234,979 B1 * 5/2001 Merzenich ............. G16H 10/20
                                                    600/559
8,532,756 B2 * 9/2013 Schalk ..................... A61B 5/16
                                                    600/545

(Continued)

FOREIGN PATENT DOCUMENTS

CN          109657642 A     4/2019
KR    10-2020-0052205 A     5/2020
KR    10-2020-0052209 A     5/2020

OTHER PUBLICATIONS

Lea Pillette et al., "Multi-Session Influence of Two Modalities of Feedback and Their Order of Presentation on MI-BCI User Training," Multimodal Technologies Interaction, 2021.
Sangin Park et al., "Improving Motor Imagery-Based Brain-Computer Interface Performance Based on Sensory Stimulation Training: An Approach Focused on Poorly Performing Users," Frontiers in Neuroscience, Nov. 5, 2021.

(Continued)

*Primary Examiner* — David E Choi

(57) ABSTRACT

Disclosed is an apparatus for a motor imagery training, which includes a measuring unit that measures a brain signal while a user performs a motor imagery training, a preprocessing unit that performs preprocessing with respect to the brain signal, a feature extraction unit that selects a time period including information related to a motor imagery from the preprocessed brain signal and calculates feature data corresponding to the brain signal of the selected time period, and a classification unit that classifies the brain signal into one of a plurality of classes based on the feature data, and the motor imagery training is any one of a first training in which the user imagines moving a body part and a second training in which the user imagines feeling a somatosensory stimuli of a tangible object using the body part.

20 Claims, 9 Drawing Sheets

(56)  References Cited

U.S. PATENT DOCUMENTS

| | | | |
|---|---|---|---|
| 10,795,441 B2 | 10/2020 | Lee et al. | |
| 11,957,475 B2 * | 4/2024 | Ushiba .................... | A61B 5/377 |
| 2010/0145214 A1 * | 6/2010 | Guan ...................... | G06F 3/015 |
| | | | 600/544 |
| 2015/0339363 A1 * | 11/2015 | Moldoveanu .......... | G09B 19/00 |
| | | | 707/723 |
| 2019/0121431 A1 * | 4/2019 | Lee ......................... | G06F 3/011 |
| 2020/0168117 A1 * | 5/2020 | P.M. Firouzabadi ........................ | |
| | | | A61B 5/7257 |
| 2024/0082533 A1 * | 3/2024 | Ortiz Catalan ....... | A61M 21/00 |
| 2024/0138748 A1 * | 5/2024 | Kim ....................... | A61B 5/378 |
| 2024/0335311 A1 * | 10/2024 | Naser ................... | A61B 5/7264 |
| 2025/0355495 A1 * | 11/2025 | Singh .................... | A61B 5/375 |

OTHER PUBLICATIONS

Lin Yao et al., "Combining Motor Imagery With Selective Sensation Toward a Hybrid-Modality BCI," IEEE Transactions on Biomedical Engineering, 2014.
Lin Yao et al., "A Stimulus-Independent Hybrid BCI Based on Motor Imagery and Somatosensory Attentional Orientation," IEEE Transactions on Neural Systems and Rehabilitation Engineering, 2017.
Natasha Padfield et al., "EEG-Based Brain-Computer Interfaces Using Motor-Imagery: Techniques and Challenges," Sensors, Mar. 22, 2019.
Byoung-Moo Ahn et al., "EEG Analysis for Design of Brain-Computer Interface(BCI)," 2010 Winter Conference of The Korean Association of Computer Education, 2010.

* cited by examiner

Left Hand          Right Hand              Right Foot 5.8cm              5.8cm                  16.5cm

APPARATUS FOR MOTOR IMAGERY TRAINING COMBINED WITH SOMATOSENSORY STIMULI AND OPERATION METHOD THEREOF

CROSS-REFERENCE TO RELATED APPLICATIONS

This application claims priority under 35 U.S.C. § 119 to Korean Patent Application No. 10-2022-0144020, filed on Nov. 1, 2022 in the Korean Intellectual Property Office, the disclosures of which are incorporated by reference herein in their entireties.

BACKGROUND

Embodiments of the present disclosure described herein relate to an apparatus for measuring and analyzing brain signals, and more particularly, relate to an apparatus for motor imagery training combined with a somatosensory stimuli, and an operating method thereof.

In the field of neuroengineering, research has been conducted on a technology that enables quadriplegic patients who cannot move to control an external driving device such as a robot arm with only thoughts by using a brain-computer interface (BCI). The brain-computer interface generally refers to acquiring and analyzing human brain signals to control computers and external devices connected thereto. Acquisition of brain signals may be performed mainly through an electroencephalogram (EEG) measurement, which is a non-invasive measurement method. In order for patients to be able to perform meaningful motions by controlling the driving device using the brain-computer interface, the driving device should be controlled in a desired position or direction.

The most important thing in this research is signal processing technology that analyzes a motor imagery of users converts the analyzed result into control signals. When the signal processing is done well, the movement intended by the user is transferred to the driving device, and the movement can be controlled to move according to the user's thoughts. Therefore, to implement various movements intended by the user, a system capable of accurately analyzing motor imagery brain signals when the user imagines the movement is essential. Existing motor image-based brain-computer interfaces show not high accuracy, and the resulting low reliability is also a problem. Recently, studies are being conducted to improve accuracy and reliability using visual, tactile, electrical, and auditory feedbacks, and studies to improve performance of a motor imagery through hybrid training combining the motor imagery and a somatosensory stimuli feedback are also being conducted.

SUMMARY

Embodiments of the present disclosure provide an apparatus for a motor imagery training combined with a somatosensory stimuli of a tangible object and an operation method thereof.

According to an embodiment of the present disclosure, an apparatus for a motor imagery training includes a measuring unit that measures a brain signal while a user performs a motor imagery training, a preprocessing unit that performs preprocessing with respect to the brain signal, a feature extraction unit that selects a time period including information related to a motor imagery from the preprocessed brain signal and calculates feature data corresponding to the brain signal of the selected time period, and a classification unit that classifies the brain signal into one of a plurality of classes based on the feature data, and the motor imagery training is any one of a first training in which the user imagines moving a body part and a second training in which the user imagines feeling a somatosensory stimuli of a tangible object using the body part.

According to an embodiment of the present disclosure, a method of operating an apparatus for a motor imagery training includes measuring a brain signal while a user performs a motor imagery training, performing preprocessing with respect to the brain signal, selecting a time period including information related to a motor imagery from the preprocessed brain signal, calculating feature data corresponding to the brain signal of the selected time period, and classifying the brain signal into one of a plurality of classes based on the feature data, and the measuring of the brain signal while the motor imagery training is performed includes measuring the brain signal during a first training in which the user imagines moving a body part, and measuring the brain signal during a second training in which the user imagines feeling a somatosensory stimuli of a tangible object using the body part.

According to an embodiment of the present disclosure, a non-transitory computer-readable medium including a program code that, when executed by a processor, causes the processor to execute operations of measuring a brain signal while a user performs a motor imagery training, performing preprocessing with respect to the brain signal, selecting a time period including information related to a motor imagery from the preprocessed brain signal, calculating feature data corresponding to the brain signal of the selected time period, and classifying the brain signal into one of a plurality of classes based on the feature data, and the measuring of the brain signal while the motor imagery training is performed includes measuring the brain signal during a first training in which the user imagines moving a body part, and measuring the brain signal during a second training in which the user imagines feeling a somatosensory stimuli of a tangible object using the body part.

BRIEF DESCRIPTION OF THE FIGURES

The above and other objects and features of the present disclosure will become apparent by describing in detail embodiments thereof with reference to the accompanying drawings.

DETAILED DESCRIPTION

Hereinafter, embodiments of the present disclosure will be described in detail and clearly to such an extent that an ordinary one in the art easily implements the present disclosure.

Components that are described in the detailed description with reference to the terms "unit", "module", "block", "~er or ~or", etc. and function blocks illustrated in drawings will be implemented with software, hardware, or a combination thereof. For example, the software may be a machine code, firmware, an embedded code, and application software. For example, the hardware may include an electrical circuit, an electronic circuit, a processor, a computer, an integrated circuit, integrated circuit cores, a pressure sensor, an inertial sensor, a microelectromechanical system (MEMS), a passive element, or a combination thereof.

Figure 1:
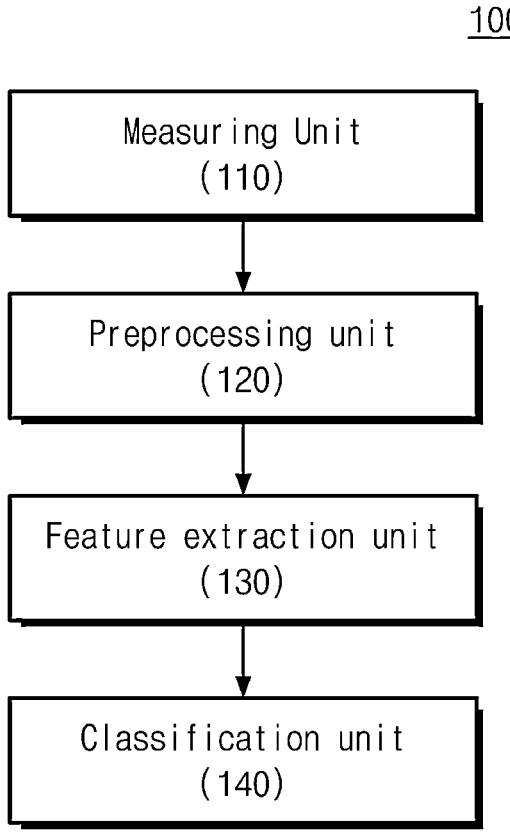
FIG. 1 is a block diagram illustrating a configuration example of an apparatus for a motor imagery training, according to an embodiment of the present disclosure.

FIG. 1 is a block diagram illustrating a configuration example of an apparatus 100 for a motor imagery training, according to an embodiment of the present disclosure. The apparatus 100 may perform a motor imagery training by measuring a brain signal when a user performs a motor imagery, extracting a feature related to a movement from the brain signal, and then classifying a user's intended movement based on the extracted feature. For example, the motor imagery of the present disclosure may include an imagery of moving a left hand, an imagery of moving a right hand, and an imagery of moving a right foot, and the apparatus 100 may classify which body part is intended to be moved. In the descriptions below, it is assumed that the body part includes the left hand, the right hand, and the right foot.

For example, the functions of the apparatus 100, for example, the functions of the artificial intelligence apparatus 100 may be implemented using devices such as combinational logic, sequential logic, one or more timers, counters, registers, state machines, one or more complex programmable logic devices (CPLD), field programmable gate arrays (FPGA), an application specific integrated circuit (ASIC), complex instruction set computer (CSIC) processors such as x86 processors, reduced instruction set computers (RISC) such as ARM processors, a central processing unit (CPU), a graphics processing unit (GPU), a neural processing unit (NPU), a TPU (tensor processing unit), an APU (accelerated processing unit), etc., which execute instructions stored in any type of memory (e.g., a flash memory such as a NAND flash memory, a low-latency NAND flash memory, a persistent memory (PMEM) such as a cross-grid non-volatile memory, a memory with large resistance change, a phase change memory (PCM), etc., or a combination thereof), or using a hardware including a combination thereof, software, or a combination thereof.

The apparatus 100 may include a measuring unit 110, a preprocessing unit 120, a feature extraction unit 130, and a classification unit 140. For example, a brain signal to be analyzed by the apparatus 100 may be acquired through an electroencephalography (EEG) measurement. An electroencephalography (EEG) may be acquired by measuring electrical signals on a scalp by attaching electrodes to the scalp, and the EEG measurement method is non-invasive, is simple, and has high temporal resolution. For a clear description below, it is assumed that the brain signal to be analyzed by the apparatus 100 according to the embodiment of the present disclosure is the EEG, but the present disclosure is not limited thereto, and the brain signal may be obtained through an electrocorticography (ECoG) measurement, or a magnetic encephalography (MEG) measurement. In particular, according to an embodiment of the present disclosure, somatosensory stimuli may be used together to perform the motor imagery training. That is, the motor imagery according to an embodiment of the present disclosure may include not only the imagery of moving the left hand, the right hand, and the right foot, but also the imagery of feeling a somatosensory stimuli of a tangible object with the left hand, the right hand, and the right foot (for example, the imagery of holding an object or the imagery of feeling a vibration of an object). A detailed motor imagery training process according to an embodiment of the present disclosure will be described in more detail with reference to FIGS. 2A to 2B.

The measuring unit 110 may measure brain signals while the user performs the motor imagery training, and may provide the measured brain signals to the preprocessing unit 120. For example, the measuring unit 110 may include at least one of a circuit or software for measuring the user's electroencephalography. For example, to measure the user's electroencephalography, the measuring unit 110 may be wired or wirelessly connected to electrodes attached to the user's scalp.

The brain signal measured by the measurer 110 may be time series data representing the level of signals over time during the user's motor imagery. For example, the time periods of the measured brain signal may correspond to elements constituting the user's motor imagery (e.g., an act of moving a body part, an act of holding a tangible object using a body part, etc.). The time interval of the time series data may be determined according to the number (e.g., 2048 Hz) of sampling per second of the measured brain signal.

For measurement of brain signals, electrodes (e.g., 64 electrodes) may be attached to the user's scalp. Depending on the position where the electrode is attached, the information that can be obtained from the measured brain signal may vary. For example, brain signals measured from electrodes attached to positions corresponding to the motor cortex or premotor cortex on the scalp may include information related to the user's movement. In addition, brain signals measured from electrodes attached to positions corresponding to the somatosensory cortex on the scalp may include information related to somatosensory stimuli felt when the object is gripped using the body part.

The preprocessing unit 120 may perform preprocessing on the user's brain signal provided from the measuring unit 110 and may provide the preprocessed brain signal to the feature extraction unit 130. The preprocessing unit 120 may perform digital filtering (e.g., infinite impulse response digital filtering) on the user's brain signal. As a result, wire noise included in the brain signal, inter-electrode signal interference, noise caused by fluorescent light, and other high-frequency band noise may be removed. For example, the preprocessing unit 120 may include at least one of circuitry or software for performing the filtering described above.

Furthermore, the preprocessing unit 120 may identify a number of artifacts caused by the user's head movement, tossing and turning, or poor attachment of electrodes during brain signal measurement, and may remove the identified artifacts from the brain signal. In addition, the preprocessing unit 120 may apply a re-referencing method (e.g., a common average reference method) to the brain signal to remove the effect of the position of the reference electrode. In addition, the preprocessing unit 120 may perform downsampling (e.g., downsampling the number of sampling per second from 2048 Hz to 256 Hz) for efficient brain signal analysis.

The feature extraction unit 130 may calculate feature data related to the user's motor imagery using the preprocessed brain signals provided by the preprocessing unit 120. In detail, the feature extraction unit 130 of the present disclosure may calculate a covariance matrix as the feature data. For example, the feature extraction unit 130 may calculate a covariance matrix from brain signals measured from electrodes attached to positions corresponding to the motor cortex, the premotor cortex, and the somatosensory cortex.

First, the feature extraction unit 130 may select a time period (e.g., a time period during which the user imagines moving a body part or imagines holding an object) corresponding to the user's motor imagery from the preprocessed brain signals, and may convert the brain signal corresponding to the selected time period into a symmetric positive-definite (SPD) matrix. For example, when the user's brain signal corresponding to the selected time period is 'X', the 'X' may be a matrix composed of 'n' rows and T columns (where, 'n' is the number of electrodes for which feature data is calculated, and 't' is the number of pieces of data included in the selected time period). Here, T may vary according to the sampling number per second of the downsampled brain signal. The normalized covariance matrix 'C' corresponding to the brain signal 'X' may be calculated as in Equation 1 below.

$$C = \frac{XX^T}{\text{trace}(XX^T)} \qquad \text{[Equation 1]}$$

The covariance matrix 'C' is composed of 'n' rows and 'n' columns, and is the normalized SPD matrix with positive eigenvalues. Thereafter, the feature extraction unit 130 uses a median absolute deviation (MAD) with respect to the covariance matrix C to arrange the covariance matrix C corresponding to each of the motor imageries on a Riemannian manifold. The Riemannian manifold refers to a topological space in which locally topological homomorphic and sufficiently uniform scalar products are defined in Euclidean space, and to which Riemannian geometry can be applied. In this case, the dimension of the Riemannian manifold is m=n(n+1)/2, and there are 'm' points P1, . . . Pm may be present on the Riemannian manifold of dimension 'm'.

A geodesic (a curve of the minimum distance connecting two points) distance $P_{distance,i,j}$ between two points $P_i$ and $P_j$ in the Riemann manifold may be calculated as in Equation 2 below.

$$P_{distance,i,j} = \left\| \text{Log}(P_i^{-1} P_j) \right\|_F \qquad \text{[Equation 2]}$$

where $\|A\|_F$ is a Frobenius norm calculated as $$\sqrt{tr(A^T A)}.$$

Using the geodesic distance between these two points, the Riemann mean $P_{mean}$ of the covariance matrices may be calculated as illustrated in Equation 3 below.

$$P_{mean} = \frac{\text{argmin}}{P \in P(n)} \sum_{i=1}^{m} P^2_{distance}(P, P_i) \qquad \text{[Equation 3]}$$

Referring at Equation 3, the Riemann mean $P_{mean}$ is the same as any point P at which the sum of squares of geodesic distances from points $P_1$, . . . $P_m$ on the Riemann manifold is minimal. In other words, the Riemann mean $P_{mean}$ may correspond to the center of mass on the Riemann manifold.

That is, the feature extraction unit 130 may calculate covariance matrices as feature data from the brain signals of a time period corresponding to the user's motor imagery performance, and may calculate the Riemann mean of the covariance matrices. In detail, since the motor imagery of the present disclosure includes a movement or a somatosensory imagery using the left hand, right hand, and right foot, respectively, covariance matrices and corresponding Riemann means may be calculated for each type of body part for the user. The feature extraction unit 130 may provide the calculated Riemann means to the classification unit 140.

The classification unit 140 may classify the measured brain signal based on the Riemann mean provided from the feature extraction unit 130. For example, the classification unit 140 may classify the user's brain signal into one of three motor imagery classes (whether it is a left hand motor imagery, a right hand motor imagery, or a right foot motor imagery) based on the Riemann mean. The classification unit 140 may include a Riemannian geometry-based classifier for performing such a classification operation.

The Riemann mean $P_{mean}$ corresponding to the covariance matrix C may correspond to the center of a class (e.g., left hand motor imagery, right hand motor imagery, and right foot motor imagery) to which the covariance matrix C belongs, and the Riemannian geometry-based classifier may calculate a distance between the center of the covariance matrices arranged on the Riemannian manifold and the reference center of each class determined in advance. That is, the distance between the Riemann mean and the reference center may reflect that the brain signal of the user corresponding to the Riemann mean is closest to which class.

In detail, the classification unit 140 may classify the user's brain signal into a class corresponding to the reference center having the minimum distance from the Riemann mean by using a Fisher geodesic minimum distance to the mean (FgMDM). For example, the reference center of each class may be determined by training the Riemannian geometry-based classifier. Depending on the classification result by the classification unit 140, accuracy of classification may also be evaluated. In particular, the classification accuracy of motor imagery brain signals combined with the somatosensory stimuli according to an embodiment of the present disclosure may be higher than the classification accuracy of motor imagery brain signals without the somatosensory stimuli.

Figure 2A:
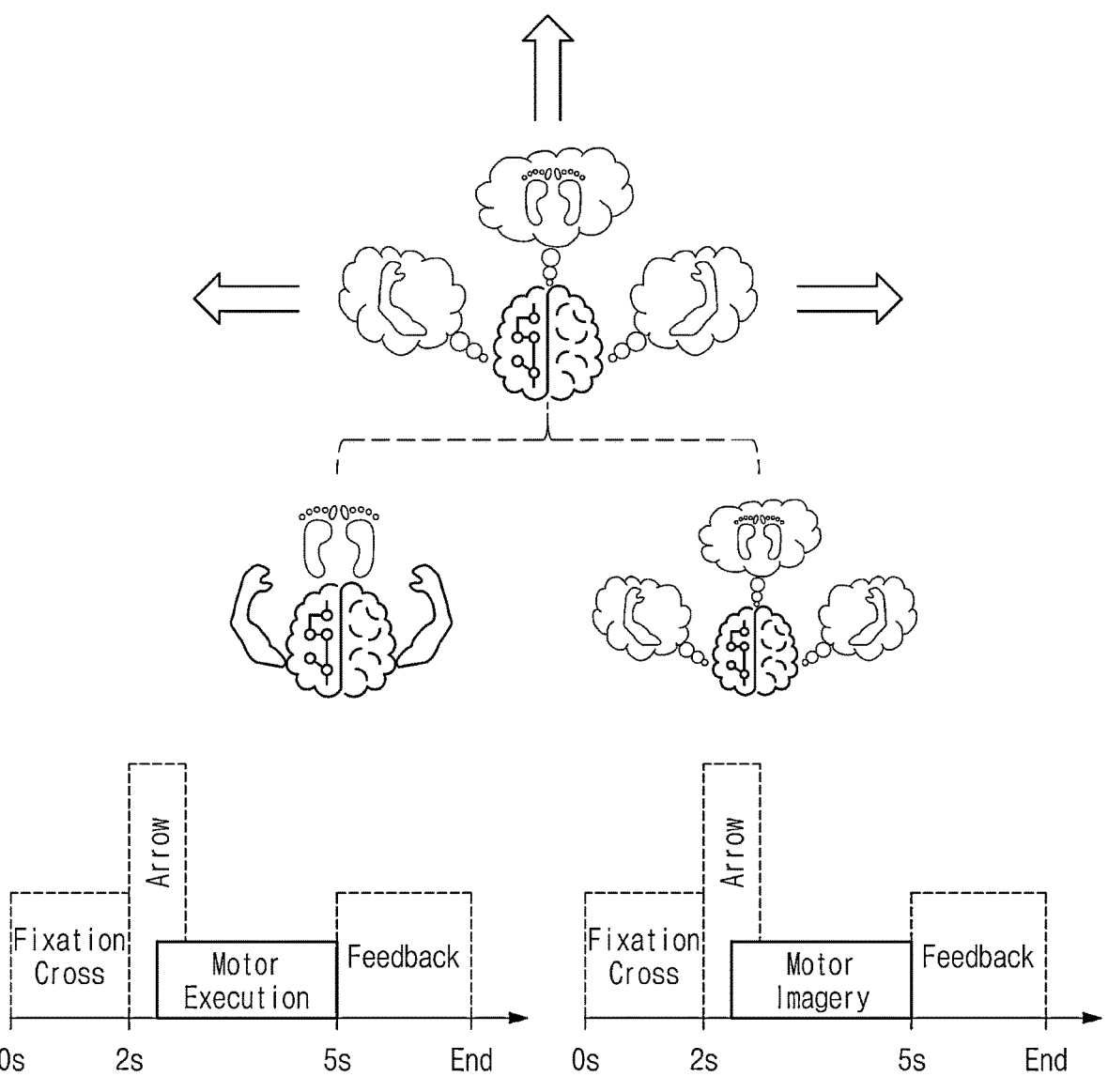
FIG. 2A illustrates an example of a process of a motor imagery training without a somatosensory stimuli.
Figure 2B:
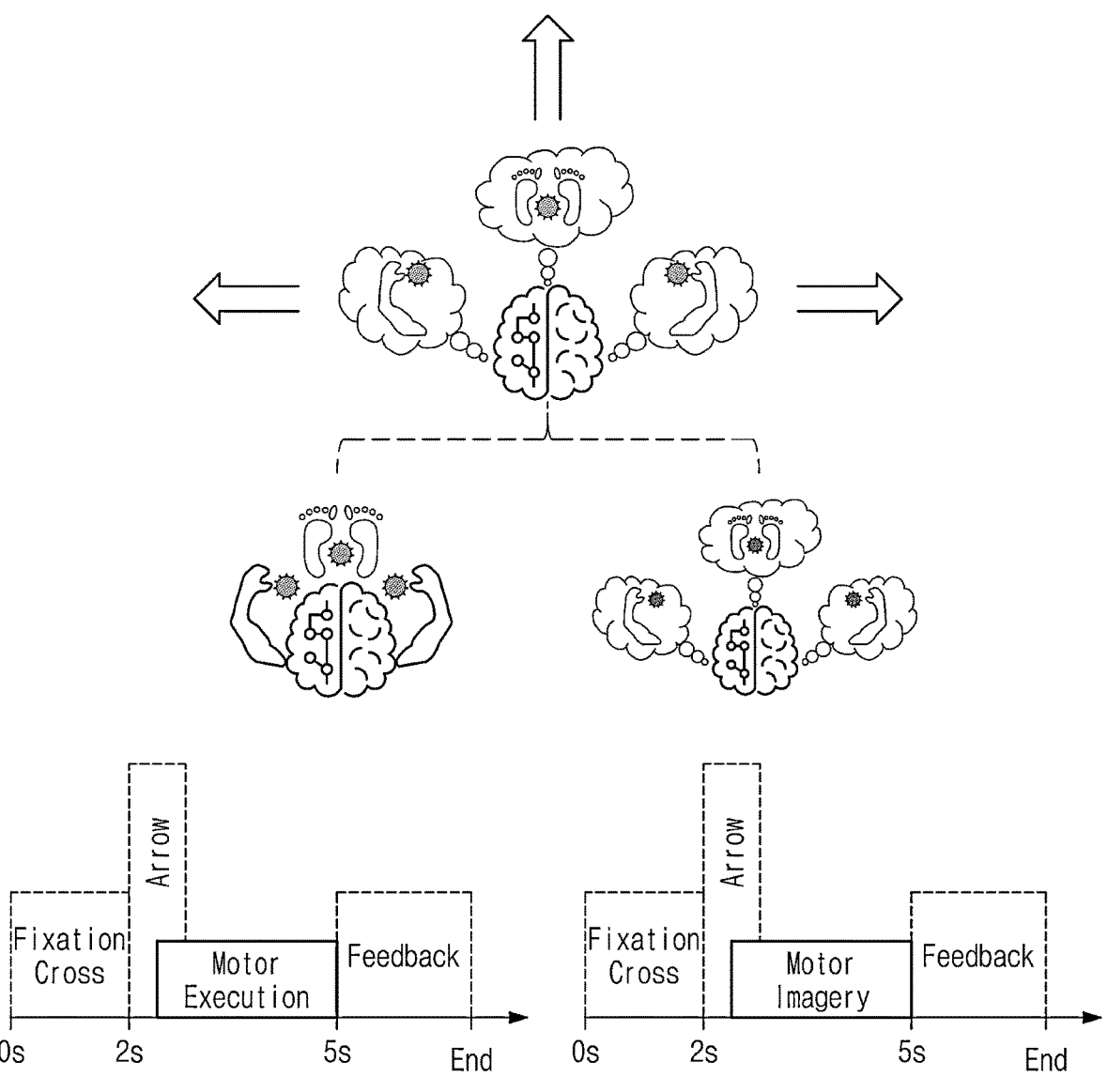
FIG. 2B illustrates an example of a process of a motor imagery training combined with a somatosensory stimuli.

FIG. 2A illustrates an example of a process of a motor imagery training without a somatosensory stimuli, and FIG. 2B illustrates an example of a process of a motor imagery training combined with a somatosensory stimuli. During the motor imagery training illustrated in FIGS. 2A and 2B, the user's brain signal may be measured (e.g., by the measuring unit 110 of FIG. 1). In both FIGS. 2A and 2B, the user may perform a motor execution task (MET) that actually moves the body part (left hand, right hand, and right foot) to facilitate the motor imagery before performing the motor imagery training.

First, referring to FIG. 2A, in the motor execution task, a user may actually move the body part according to an arrow displayed on a monitor. For example, a fixation cross may be output on the monitor for 2 seconds, during which the user's brain signal may correspond to a resting state. Then, one of a left arrow (corresponding to the user's left hand), a right arrow (corresponding to the user's right hand), and a front arrow (corresponding to the user's right foot) may be displayed on the monitor, and the user may move the corresponding body part within 3 seconds after the arrow is displayed. After the user moves the body part, a brain activity related to the corresponding movement is output as a neurofeedback, and this process is repeated a predetermined number of times until the motor execution task is completed.

After the motor execution task is completed, the user may perform a motor imagery task (MIT). The motor imagery task proceeds similarly to the motor execution task described above. When a fixation cross is displayed on the monitor for 2 seconds and then one of the left arrow, right arrow, and front arrow is displayed, the user may imagine (for example, imagining moving the user's left hand, imagining moving the user's right hand, or imagining moving the user's right foot) moving the corresponding body part within 3 seconds.

Referring now to FIG. 2B, a motor execution task may be combined with the somatosensory stimuli. In detail, the somatosensory stimuli used in the present disclosure may be one of a somatosensory stimuli generated when a tangible object is grasped using the body part or a somatosensory stimuli generated when a vibration of an object is felt through the body part. Although FIG. 2B illustrates that the motor execution and the motor imagery are performed using the somatosensory stimuli generated when the object is grasped, the present disclosure is not limited thereto, and the motor execution and the motor imagery illustrated in FIG. 2B may also be performed using the somatosensory stimuli generated when a vibration is felt. For convenience of the description, in this specification, the motor execution and the motor imagery are described on the basis of being performed using the somatosensory stimuli generated when holding an object, but the case of using the somatosensory stimuli generated when feeling the vibration of an object may also be performed in the same way.

In the motor execution task of FIG. 2B, when a fixation cross is output on the monitor for 2 seconds, and then one of the left arrow, right arrow, and front arrow is output, the user may grasp the object using the corresponding body part within 3 seconds. After the user grasps the object, brain activity related to the corresponding somatosensory stimuli is output as the neurofeedback, and this process is repeated a predetermined number of times until the motor execution task is completed.

As in FIG. 2A, after the motor execution task is completed, the user may perform the motor imagery task. The motor imagery task of FIG. 2B may also be combined with the somatosensory stimuli, and the user may imagine holding a tangible object with a corresponding body part within 3 seconds after the arrow is displayed.

In each brain signal measured while performing the motor imagery task illustrated in FIGS. 2A and 2B, information related to motor imagery performance may be included within 2 to 5 seconds after the cross mark is output. Therefore, the feature extraction unit 130 of FIG. 1 may select an arbitrary time period (e.g., a time period corresponding to 2.4 seconds to 4.4 seconds) within 2 seconds to 5 seconds of the user's brain signal to perform the above-described Riemann geometry analysis.

In detail, information related to imagining moving the body part may be included in the 2 to 5 second time period of the brain signal measured while performing the motor imagery task illustrated in FIG. 2A, and information related to imagining moving the body part as well as information related to imagining holding the object using the body part may be included in the 2 to 5 second time period of the brain signal measured while performing the motor imagery task illustrated in FIG. 2B. That is, by comparing the brain signal measured while performing the task of FIG. 2A with the brain signal measured while performing the task of FIG. 2B, the effect of the somatosensory stimuli on the accuracy of motor imagery may be found. The motor imagery brain signal measured in this way may be used to drive an external device.

Figure 3:
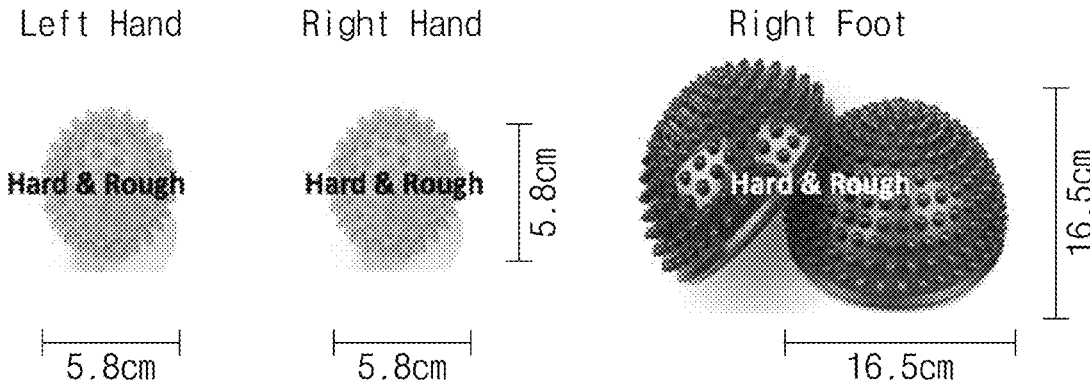
FIG. 3 illustrates an example of a tangible object used in a motor imagery training in which somatosensory stimuli is combined.

FIG. 3 illustrates an example of a tangible object used in a motor imagery training in which somatosensory stimuli is combined. An object held by the left and right hands is a hard and rough ball with a diameter of 5.8 cm, and an object held by the right foot is a hard and rough ball with a diameter of 16.5 cm. For the object grasped with the right foot, only half of the ball is used.

Figure 4:
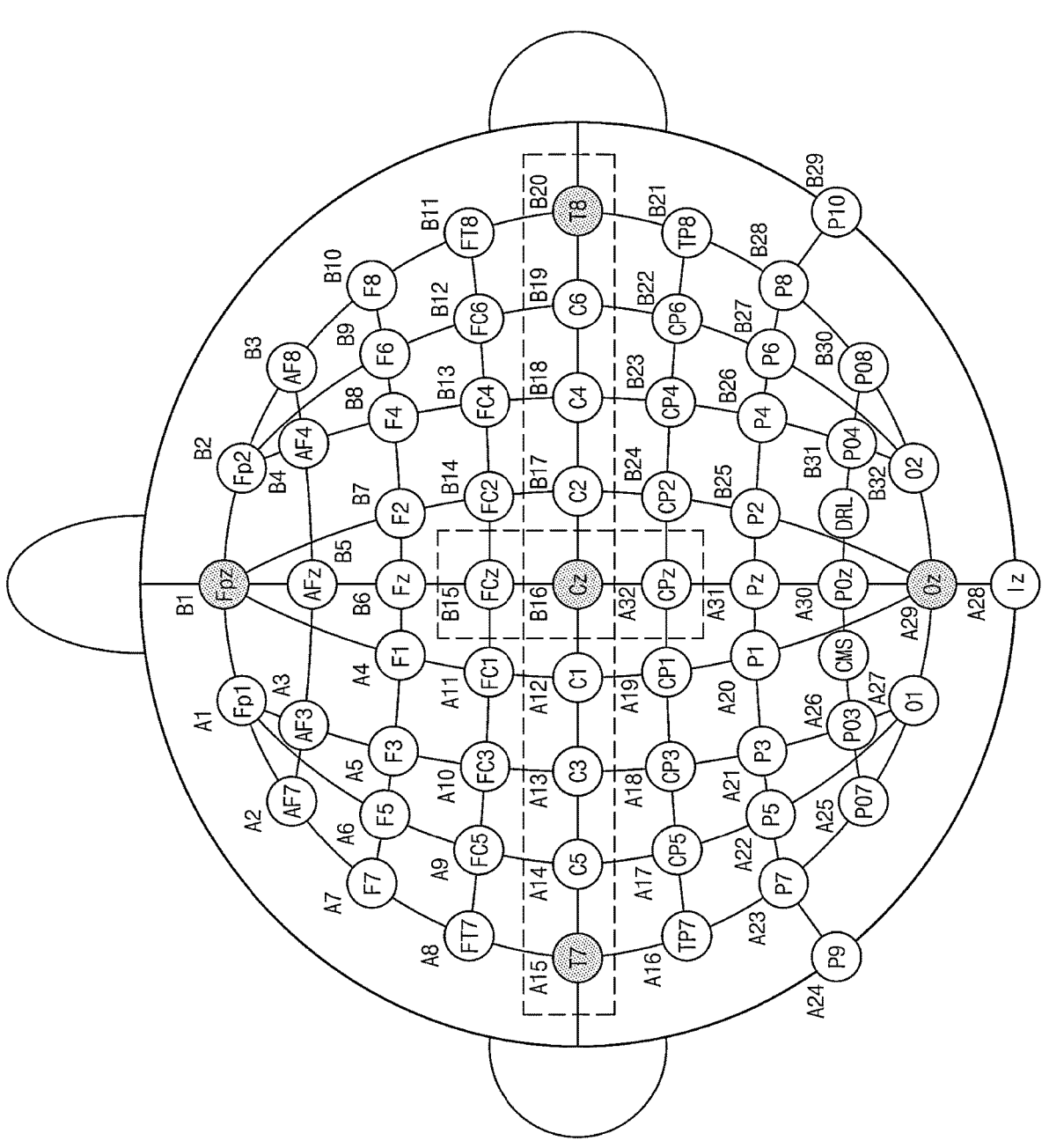
FIG. 4 illustrates an example of positions of electrodes attached when brain signals are measured.

FIG. 4 illustrates an example of positions of electrodes attached when brain signals are measured. FIG. 4 illustrates a general 64-channel 10-20 system used for EEG measurement. Among the 64 electrodes, in the analysis process according to the embodiment of the present disclosure, electrodes attached to positions corresponding to the motor cortex, the premotor cortex, and the somatosensory cortex on the scalp are selected. In detail, the brain signals measured from electrodes C1 to C6 of the central region and the electrodes before and after the central region may include information related to the motion and somatosensory. For example, the selected electrodes may be FCz, C1, C3, C5, T7, Cz, C2, C4, C6, T8, and CPz (indicated by a red dotted line). However, the present disclosure is not limited thereto, and electrodes other than those described above may be selected for analysis, and electrodes having a different number from those of FIG. 4 may be attached to other positions.

Figure 5:
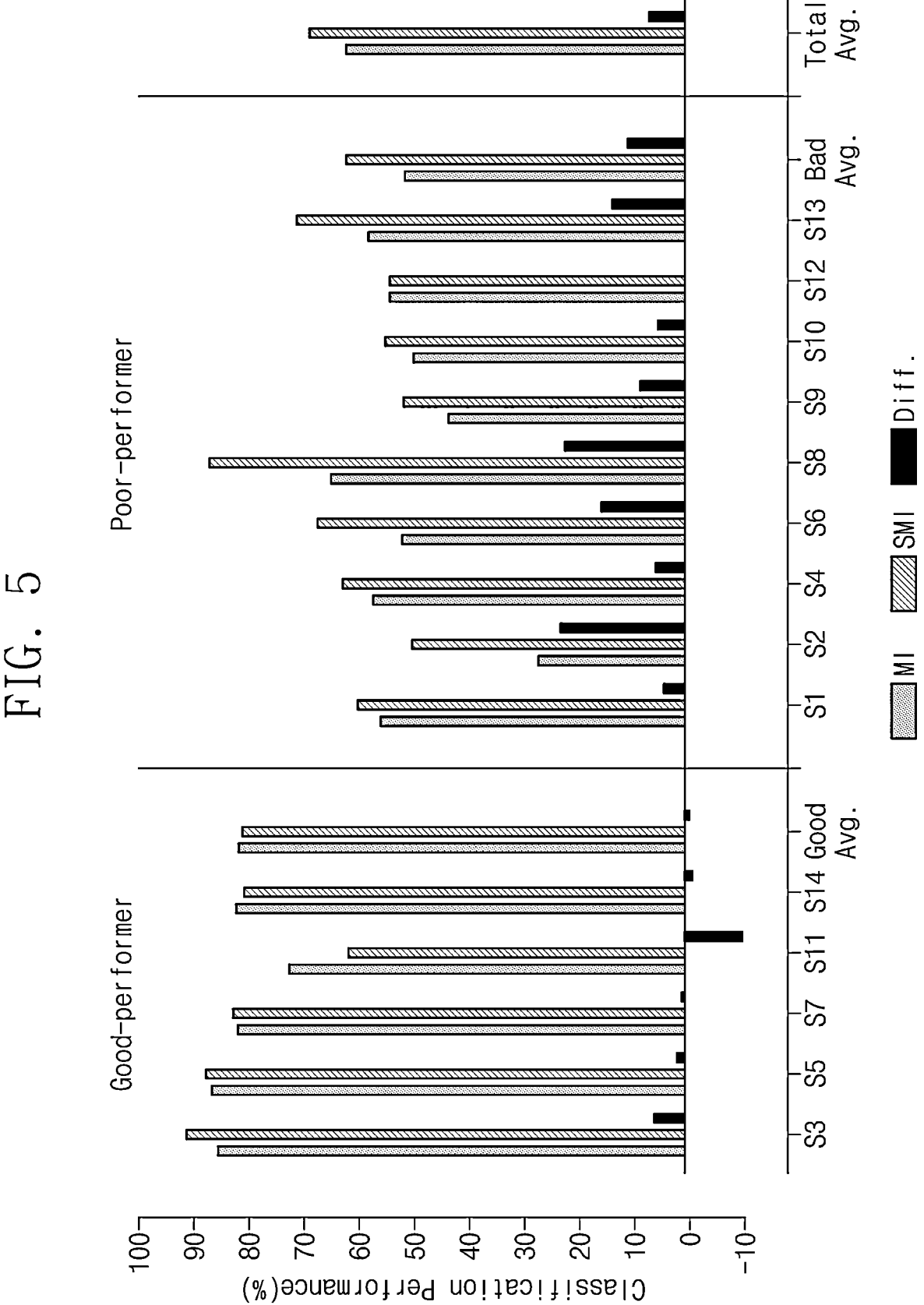
FIG. 5 illustrates classification accuracy of motor imagery brain signals, according to an embodiment of the present disclosure.

FIG. 5 illustrates classification accuracy of motor imagery brain signals, according to an embodiment of the present disclosure. Referring to FIG. 5, the classification accuracy of motor imagery (MI) and motor imagery (SMI) combined with the somatosensory stimuli is illustrated with respect to 14 users S1 to S14. In this case, users (S3, S5, S7, S11, and S14) of which the classification accuracy of motor imagery (MI) without somatosensory stimuli is equal to or greater than a predetermined threshold value (e.g., 70%) are classified as good-performers, and users (S1, S2, S4, S6, S8, S9, S10, S12, and S13) whose classification accuracy is less than the predetermined threshold value (e.g., 70%) are classified as poor-performers. As a result of calculating the average of the classification accuracy of all subjects, the accuracy of motor imagery (SMI) combined with the somatosensory stimuli is higher than that of the motor imagery (MI) without the somatosensory stimuli. In particular, the accuracy of SMI combined with the somatosensory stimuli is higher than the poor-performers. In other words, for users who are not familiar with existing motor imagery, the effect of motor imagery training combined with the somatosensory stimuli is greater. Therefore, motor imagery training combined with the somatosensory stimuli has an effect of increasing the motor imagery accuracy of a user with low motor imagery accuracy.

Figure 6A:
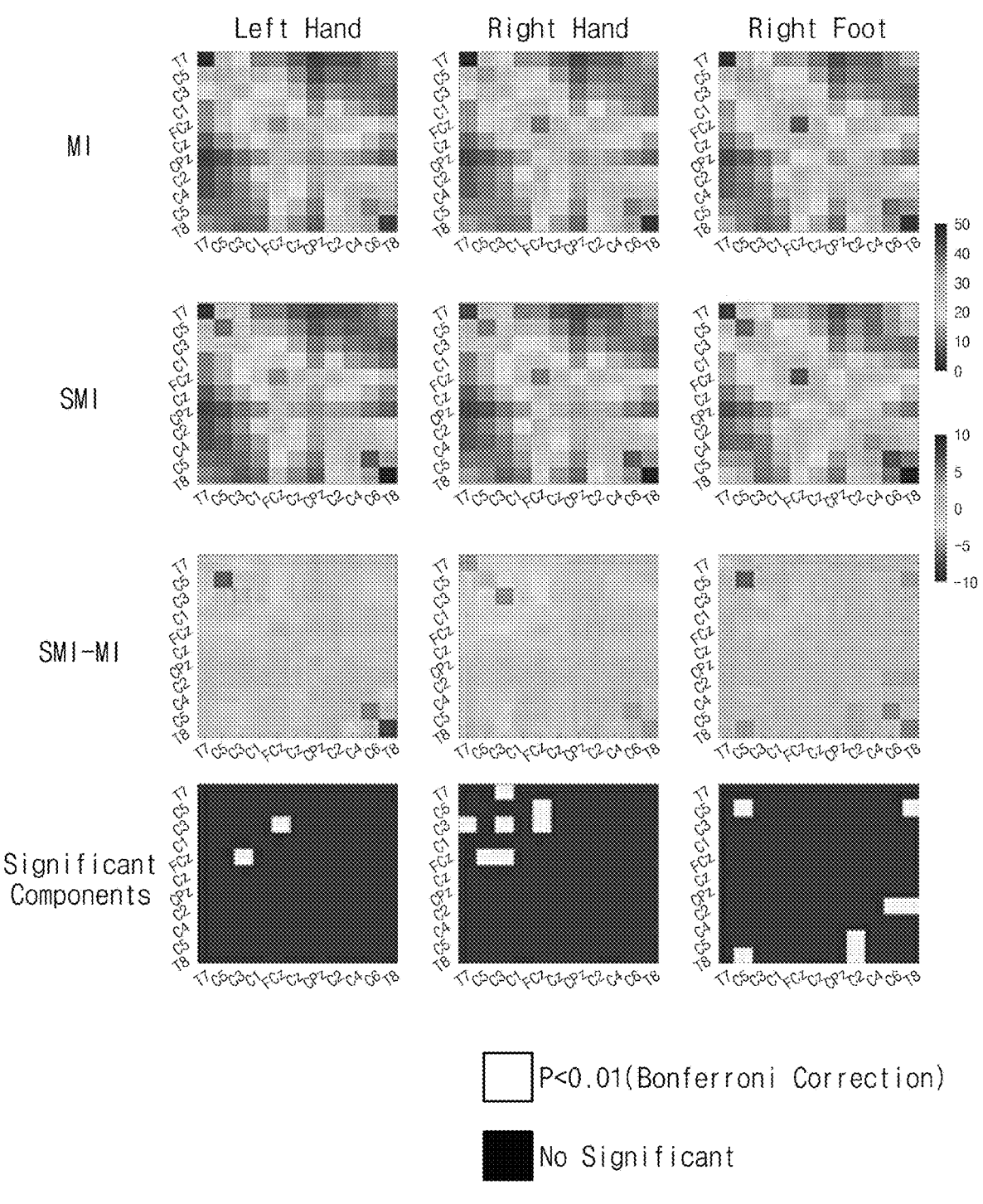
FIG. 6A illustrates an example of a heat map corresponding to a covariance matrix calculated from brain signals of a good-performer of FIG. 5.
Figure 6B:
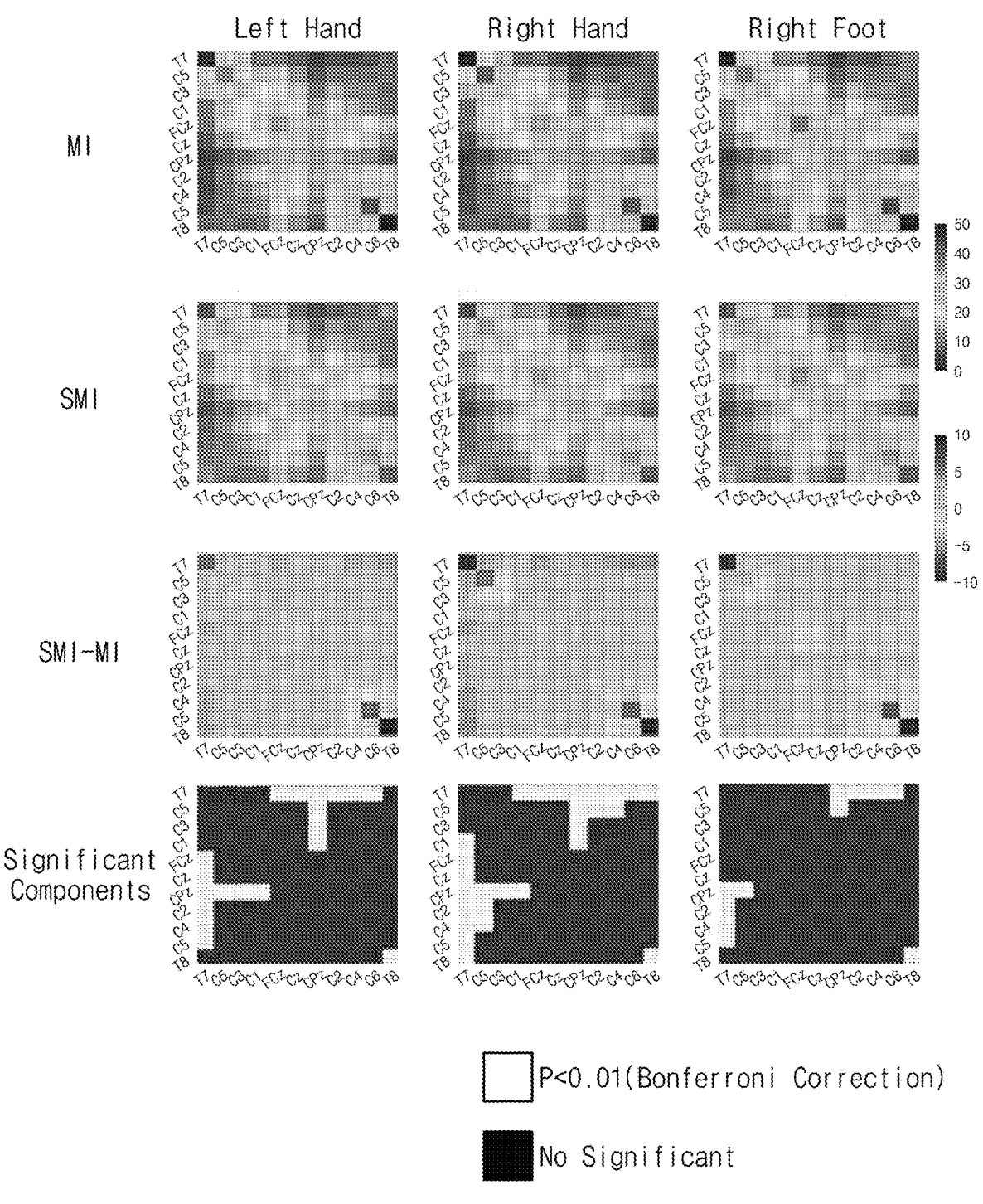
FIG. 6B illustrates an example of a heat map corresponding to a covariance matrix calculated from brain signals of a poor-performer of FIG. 5.

FIG. 6A illustrates an example of a heat map corresponding to a covariance matrix calculated from brain signals of a good-performer of FIG. 5, and FIG. 6B illustrates an example of a heat map corresponding to a covariance matrix calculated from brain signals of a poor-performer of FIG. 5. Referring to FIGS. 6A and 6B, each of covariance matrices corresponding to the brain signals of motor imageries of the left hand, right hand, and right foot (including both motor imagery (MI) without the somatosensory stimuli and motor imagery (SMI) combined with the somatosensory stimuli) may be expressed as a heat map, and since each covariance matrix is a symmetric positive definite (SPD) matrix as described with reference to FIG. 1, each corresponding heat map is also represented in a symmetrical form around the diagonal.

In addition, a difference (MI-SMI) between a covariance matrix of the motor imagery (MI) brain signal without the somatosensory stimuli and a covariance matrix of the motor imagery (SMI) brain signal combined with the somatosensory stimuli may be calculated. Referring to the MI-SMI heat map, it is possible to find out the difference in brain activity according to the presence or absence of the somatosensory stimuli, and to find out the electrodes (significant components) in which the difference is significant. As described with reference to FIG. 5, when comparing FIGS. 6A and 6B, a difference between the MI heatmap and the SMI heatmap is larger in the poor-performer than in the good-performer.

Figure 7:
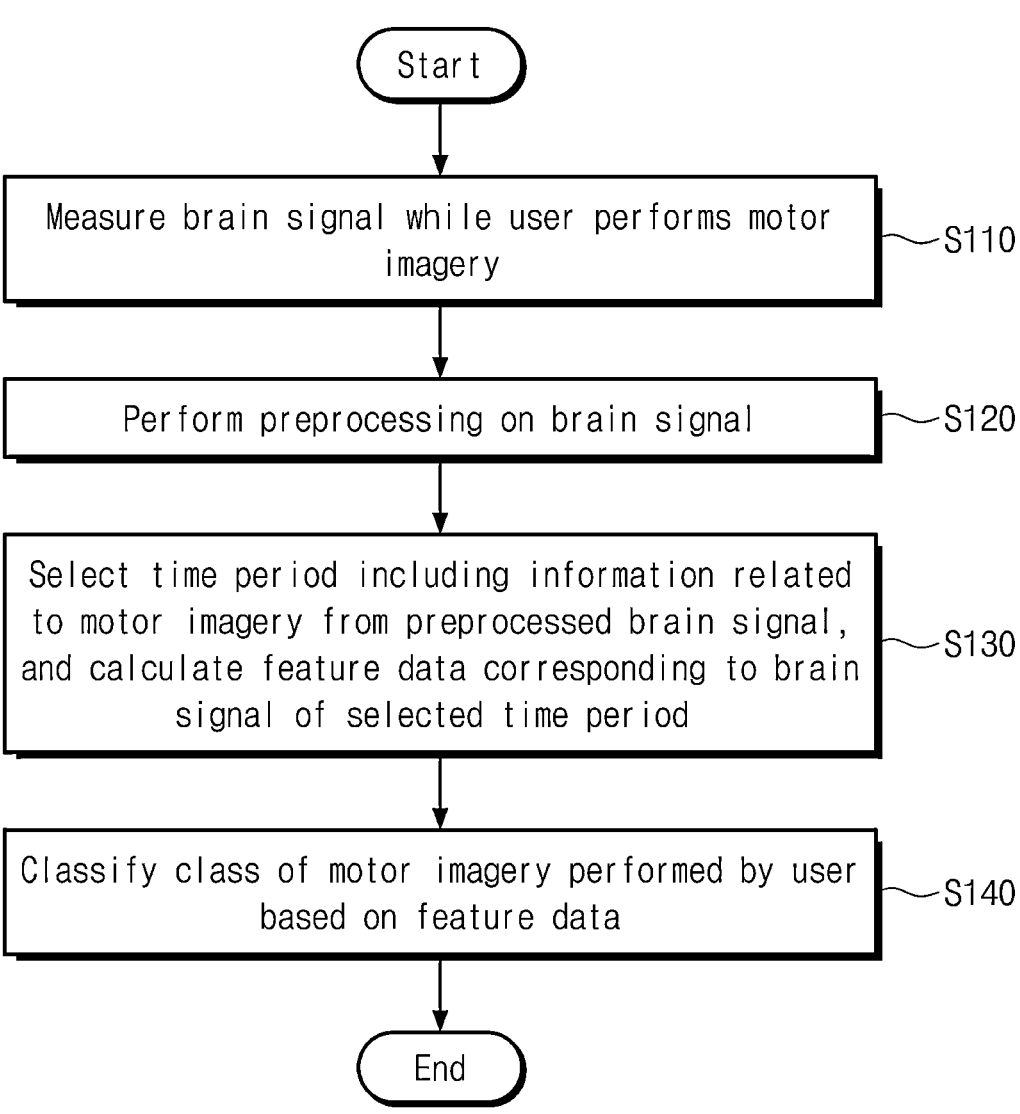
FIG. 7 is a flowchart illustrating an example of a method of operating an apparatus for a motor imagery training, according to an embodiment of the present disclosure.

FIG. 7 is a flowchart illustrating an example of a method of operating an apparatus for a motor imagery training, according to an embodiment of the present disclosure. Hereinafter, it will be described with reference to FIG. 1 together with FIG. 7.

In operation S110, the measuring unit 110 may measure the brain signal while the user performs the motor imagery. In operation S120, the preprocessing unit 120 may perform preprocessing on the measured brain signal. In operation S130, the feature extraction unit 130 may select a time period including information related to the motor imagery from the preprocessed brain signal, and calculate feature data corresponding to the brain signal of the selected time period. For example, the feature extraction unit 130 may calculate a covariance matrix corresponding to the brain signal of the selected time period, may arrange the covariance matrix on the Riemann manifold, and may calculate the Riemann mean corresponding to the covariance matrix. For example, the covariance matrix may be calculated according to Equation 1, and the Riemann mean may be calculated according to Equations 2 and 3. In operation S140, the classification unit 140 may classify the class of motor imagery performed by the user based on the feature data (e.g., Riemann mean).

Furthermore, the motor imagery training method according to an embodiment of the present disclosure may be implemented with program codes stored in a non-transitory computer readable medium. For example, a non-transitory computer-readable media may be included on a magnetic media, an optical media, or a combination thereof (e.g., CD-ROM, hard drive, read-only memory, flash drive, etc.).

For example, the non-transitory computer readable medium may include a program code that, when executed by a processor, causes the processor to measure a brain signal while a user performs a motor imagery, to perform preprocessing on the brain signal, to select a time period including information related to the motor imagery from the preprocessed brain signal, to calculate feature data corresponding to the brain signal of the selected time period, and to classify classes of the motor imagery performed by the user based on the feature data.

According to an embodiment of the present disclosure, high-quality data related to a motor imagery may be obtained. In addition, according to an embodiment of the present disclosure, the accuracy of a motor imagery classification may be improved by combining somatosensory stimuli.

The above description refers to embodiments for implementing the present disclosure. Embodiments in which a design is changed simply or which are easily changed may be included in the present disclosure as well as an embodiment described above. In addition, technologies that are easily changed and implemented by using the above embodiments may be included in the present disclosure. Accordingly, the scope of the present disclosure should not be limited to the above-described embodiments and should be defined by equivalents of the claims as well as the claims to be described later.

STATEMENT REGARDING PRIOR DISCLOSURES BY THE INVENTOR OR A JOINT INVENTOR

The inventors of the present application have made related disclosure in Sangin Park et al. "Improving Motor Imagery-Based Brain-Computer Interface Performance Based on Sensory Stimulation Training: An Approach Focused on Poorly Performing Users," Frontiers in Neuroscience, Nov. 5, 2021. The related disclosure was made less than one year before the effective filing date (Nov. 1, 2022) of the present application and the inventors of the present application are the same as those of the related disclosure. Accordingly, the related disclosure is disqualified as prior art under 35 USC 102(a)(1) against the present application. See 35 USC 102(b)(1)(A).

What is claimed is:

1. An apparatus comprising:

a measuring unit configured to measure a brain signal while a user performs a motor imagery training;

a preprocessing unit configured to perform preprocessing with respect to the brain signal;

a feature extraction unit configured to select a time period including information related to a motor imagery from the preprocessed brain signal and to calculate feature data corresponding to the brain signal of the selected time period; and a classification unit configured to classify the brain signal into one of a plurality of classes based on the feature data, and wherein the motor imagery training is:

any one of a first training in which the user imagines moving a body part and a second training in which the user imagines feeling a somatosensory stimuli of a tangible object using the body part.

2. The apparatus of claim 1, wherein the body part includes a left hand, a right hand, and a right foot of the user, and wherein the plurality of classes include the motor imagery of the left hand, the motor imagery of the right hand, and the motor imagery of the right foot.

3. The apparatus of claim 1, wherein the somatosensory stimuli is any one of a somatosensory sensation generated when holding the tangible object and a somatosensory sensation generated when feeling a vibration of the tangible object.

4. The apparatus of claim 1, wherein the first training includes:

a first step in which the user moves the body part; and a second step of imagining that the user moves the body part.

5. The apparatus of claim 4, wherein the first step includes a period in which the brain signal of the user corresponds to a resting state, a period in which the user moves the body part, and a period in which a neurofeedback related to a movement of the body part is provided to the user, and the second step includes a period in which the brain signal of the user corresponds to a resting state, a period in which the user imagines moving the body part, and a period in which a neurofeedback related to the imagery is provided to the user.

6. The apparatus of claim 1, wherein the second training includes:

a first step in which the user feels the somatosensory stimuli of the tangible object using the body part; and a second step in which the user imagines feeling the somatosensory stimuli of the tangible object using the body part.

7. The apparatus of claim 6, wherein the first step includes a period in which the brain signal of the user corresponds to a resting state, a period in which the user feels the somatosensory stimuli of the tangible object using the body part, and a period in which a neurofeedback related to the somatosensory stimuli is provided to the user, and the second step includes a period in which the brain signal of the user corresponds to a resting state, a period in which the user imagines feeling the somatosensory stimuli of the tangible object using the body part, and a period in which a neurofeedback related to the imagery is provided to the user.

8. The apparatus of claim 1, wherein the measuring unit measures both a first brain signal corresponding to the first training of the user and a second brain signal corresponding to the second training of the user, and wherein, when a first accuracy with which the classification unit classifies the first brain signal of the user into the plurality of classes is less than a predetermined threshold value, a second accuracy with which the classification unit classifies the second brain signal of the user into the plurality of classes is higher than the first accuracy.

9. The apparatus of claim 1, wherein the preprocessing unit performs digital filtering on the brain signal, applies a re-standard method to the brain signal, performs downsampling on the brain signal, and removes artifacts of the brain signal.

10. A method of operating an apparatus for a motor imagery training, the method comprising;

measuring a brain signal while a user performs a motor imagery training;

performing preprocessing with respect to the brain signal;

selecting a time period including information related to a motor imagery from the preprocessed brain signal;

calculating feature data corresponding to the brain signal of the selected time period; and classifying the brain signal into one of a plurality of classes based on the feature data, and wherein the measuring of the brain signal while the motor imagery training is performed includes:

measuring the brain signal during a first training in which the user imagines moving a body part; and

12 measuring the brain signal during a second training in which the user imagines feeling a somatosensory stimuli of a tangible object using the body part.

11. The method of claim 10, wherein the body part includes a left hand, a right hand, and a right foot of the user, and wherein the plurality of classes include the motor imagery of the left hand, the motor imagery of the right hand, and the motor imagery of the right foot.

12. The method of claim 10, wherein the somatosensory stimuli is any one of a somatosensory sensation generated when holding the tangible object and a somatosensory sensation generated when feeling a vibration of the tangible object.

13. The method of claim 10, wherein the measuring of the brain signal while the first training is performed includes:

measuring the brain signal while the user moves the body part; and measuring the brain signal while the user imagines moving the body part.

14. The method of claim 13, wherein the measuring of the brain signal while the user moves the body part includes:

adjusting the brain signal of the user to correspond to a resting state;

moving the body part by the user; and providing a neurofeedback related to the movement of the body part to the user, and wherein the measuring of the brain signal while the user imagines moving the body part includes:

adjusting the brain signal of the user to correspond to a resting state;

imagining moving the body part by the user; and providing a neurofeedback related to the imagery to the user.

15. The method of claim 10, wherein the measuring of the brain signal while the second training is performed includes:

measuring the brain signal while the user feels the somatosensory stimuli of the tangible object using the body part; and measuring the brain signal while the user imagines feeling the somatosensory stimuli of the tangible object using the body part.

16. The method of claim 15, wherein the measuring of the brain signal while the user feels the somatosensory stimuli of the tangible object using the body part includes:

adjusting the brain signal of the user to correspond to a resting state;

feeling the somatosensory stimuli of the tangible object using the body part by the user; and providing a neurofeedback related to the imagery to the user, and wherein the measuring of the brain signal while the user imagines feeling the somatosensory stimuli of the tangible object using the body part includes:

adjusting the brain signal of the user to correspond to a resting state;

imagining that the user feels the somatosensory stimuli of the tangible object using the body part; and providing a neurofeedback related to the imagery to the user.

17. The method of claim 10, wherein, when the first accuracy in which the first brain signal of the user is classified into the plurality of classes is less than a predetermined threshold value, a second accuracy in which the second brain signal of the user is classified into the plurality of classes is higher than the first accuracy.

18. The method of claim 10, wherein the performing of the preprocessing includes:

performing a digital filtering on the brain signal;

applying a re-standard method to the brain signal;

performing a downsampling on the brain signal; and removing artifacts of the brain signal.

19. A non-transitory computer-readable medium comprising a program code that, when executed by a processor, causes the processor to execute operations of:

measuring a brain signal while a user performs a motor imagery training;

performing preprocessing with respect to the brain signal;

selecting a time period including information related to a motor imagery from the preprocessed brain signal;

calculating feature data corresponding to the brain signal of the selected time period; and classifying the brain signal into one of a plurality of classes based on the feature data, and wherein the measuring of the brain signal while the motor imagery training is performed includes:

measuring the brain signal during a first training in which the user imagines moving a body part; and measuring the brain signal during a second training in which the user imagines feeling a somatosensory stimuli of a tangible object using the body part.

20. The non-transitory computer-readable medium of claim 19, wherein, when a first accuracy in which the first brain signal of the user is classified into the plurality of classes is less than a predetermined threshold value, a second accuracy in which the second brain signal of the user is classified into the plurality of classes is higher than the first accuracy.

\* \* \* \* \*